United States Patent [19]
Lantzsch et al.

[11] Patent Number: 4,792,606
[45] Date of Patent: Dec. 20, 1988

[54] PROCESS FOR THE PREPARATION OF DIMERIC AROMATIC ACYL CYANIDES

[75] Inventors: Reinhard Lantzsch, Wuppertal; Hermann-Dieter Krall, Duesseldorf, both of Fed. Rep. of Germany

[73] Assignee: Bayer Aktiengesellschaft, Leverkusen, Fed. Rep. of Germany

[21] Appl. No.: 74,384

[22] Filed: Jul. 16, 1987

[30] Foreign Application Priority Data

Aug. 5, 1986 [DE] Fed. Rep. of Germany ....... 3626411

[51] Int. Cl.⁴ .............. C07D 401/12; C07D 405/12; C07D 403/12; C07D 409/12; C07D 417/12; C07D 213/46; C07D 213/57; C07D 239/34; C07D 239/26; C07D 277/30; C07D 333/38; C07D 307/54; C07D 317/60; C07D 319/08; C07C 121/62; C07C 121/68

[52] U.S. Cl. ................... 544/296; 544/300; 544/301; 544/335; 544/334; 544/310; 544/311; 544/316; 544/317; 544/320; 544/321; 544/319; 544/323; 544/324; 544/328; 544/329; 544/327; 544/255; 544/331; 544/332; 544/333; 544/230; 558/399; 558/344; 558/350; 558/351; 546/115; 546/116; 546/18; 546/19; 546/263; 546/280; 546/284; 546/283; 546/318; 546/326; 546/327; 546/287; 546/296; 546/297; 546/298; 546/307; 546/310; 546/301; 546/302; 546/312; 546/330; 548/183; 548/184; 548/187; 548/188; 548/10; 548/191; 548/194; 548/198; 548/201; 548/204; 548/213; 548/214; 548/147; 548/153; 549/331; 549/332; 549/334; 549/350; 549/363; 549/365; 549/359; 549/360; 549/364; 549/373; 549/347; 549/370; 549/349; 549/336; 549/337; 549/338; 549/339; 549/340; 549/341; 549/342; 549/448; 549/449; 549/450; 549/451; 549/473; 549/474; 549/476; 549/478; 549/479; 549/480; 549/481; 549/482; 549/484; 549/485; 549/488; 549/494; 549/495; 549/496

[58] Field of Search .............. 544/296, 300, 301, 310, 544/317, 319, 328, 331, 335, 311, 320, 323, 329, 332, 334, 316, 321, 324, 327, 333, 230, 255; 546/263, 283, 327, 297, 310, 312, 280, 318, 287, 298, 301, 330, 284, 326, 296, 307, 302, 115, 116, 18, 19; 548/183, 188, 194, 204, 147, 184, 190, 198, 213, 153, 187, 191, 201, 214; 558/339, 344, 350, 351; 549/331, 332, 334, 350, 363, 365, 359, 360, 364, 365, 373, 347, 370, 349, 336, 337, 338, 339, 340, 341, 342, 448, 449, 450, 451, 473, 474, 476, 478, 479, 480, 481, 482, 484, 485, 488, 494, 495, 496

[56] References Cited

U.S. PATENT DOCUMENTS

3,134,803  5/1964  Arnold et al. .................... 260/465.4

FOREIGN PATENT DOCUMENTS

76957  4/1983  European Pat. Off. .

OTHER PUBLICATIONS

Westwood et al., Chemistry and Industry, 1970, 1408/1409, (Oct. 31, 1970).
Koenig et al., Tetrahedron Letters, 1974, No. 26, pp. 2275-2278.
Ando et al., Synthesis, 1983, No. 8, pp. 637; 638.
Diels et al., "Berichte", vol. 41, pp. 1893-1901, (1908).

Primary Examiner—John M. Ford
Attorney, Agent, or Firm—Sprung Horn Kramer & Woods

[57] ABSTRACT

A process for the preparation of a dimeric aromatic acyl cyanide of the formula

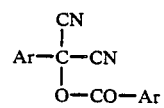

in which
  Ar is optionally substituted phenyl, naphthyl or hetaryl,
comprising reaction an acyl halide of the formula

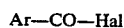

in which
  Hal is fluorine, chlorine or bromine, with an alkali metal cyanide in a two-phase system comprising water and a water-immiscible or only sparingly water-miscible aliphatic ketone, and in the presence of a phase-transfer catalyst. The products are known intermediates for pesticides.

6 Claims, No Drawings

PROCESS FOR THE PREPARATION OF DIMERIC AROMATIC ACYL CYANIDES

The present invention relates to a new process for the preparation of known dimeric aromatic acyl cyanides.

Whereas aliphatic acyl cyanides dimerize very easily and, in some cases, even spontaneously, dimeric aromatic acyl cyanides cannot readily be prepared by dimerization. As is known, their preparation in pure form is connected with difficulties.

1. The reaction of aromatic acyl chlorides with liquid hydrocyanic acid and pyridine is known; Berichte 41, 1893 (1908).

However, the handling of the toxic hydrocyanic acid on an industrial scale is not without problems. Furthermore, pyridine is expensive and difficult to recover. In addition, the yields achieved are below 60 percent of theory. The same is true for the reaction of aromatic acid anhydrides with hydrocyanic acid. (In this respect, see U.S. Patent Specification 3,134,803).

2. The conventional method of synthesis of dimeric acyl cyanide is the reaction of acyl chlorides with alkali metal cyanides in aqueous solution.

However, this method cannot be used generally, and the dimeric acyl cyanides are usually obtained in poor yields, since monomeric acyl cyanides, carboxylic acids or carboxylic acid anhydrides can also be produced.

Literature citations:

Chemistry and Industry 1970, 1408 (yields between 20 and 50%) Tetrahedron Letters 1974, 26, 2275 (maximum yield 46%) Synthesis 1983, 8, 638 (maximum yield 15%).

In Chemistry and Industry 1970, 1408, it is reported that only o-substituted acyl chlorides and unsubstituted benzoyl chloride react to form dimeric acyl cyanides.

Dimeric acyl cyanides prepared according to Tetrahedron Letters 1974, 2275 are heavily contaminated with the corresponding benzoic acid.

There is, therefore, a need for commercially practical processes for the preparation of dimeric aromatic acyl cyanides.

It has been found that dimeric aromatic acyl cyanides of the general formula $$\begin{array}{c} CN \\ | \\ Ar-C-CN \\ | \\ O-CO-Ar \end{array} \quad (I)$$

in which

Ar represents optionally substituted phenyl, naphthyl or hetaryl, are obtained when acyl halides of the general formula $$Ar-CO-Hal \quad (II)$$

in which

Ar has the abovementioned meaning and Hal represents fluorine, chlorine or bromine, are reacted with alkali metal cyanides in a two-phase system comprising water and a water-immiscible or sparingly water-miscible aliphatic ketone and in the presence of a phase-transfer catalyst.

It is to be described as extremely surprising that very pure dimeric aromatic acyl cyanides are produced in high yield according to the reaction according to the invention since, according to Tetrahydron Letters 1974, 2275, for example, only significantly lower yields result and the dimeric acyl cyanides, contaminated by the carboxylic acids, only have a content of about 80-85% under similar reaction conditions. Purification is only achieved with difficulty and is connected with large losses.

If 3,4-dichlorobenzoyl chloride is used as the acyl halide of the formula (II), sodium cyanide is used as the alkali metal cyanide, methyl isobutyl ketone is used as the aliphatic ketone, and triethylbenzylammonium chloride is used as the phase-transfer catalyst, the course of the reaction may be represented by the following equation:

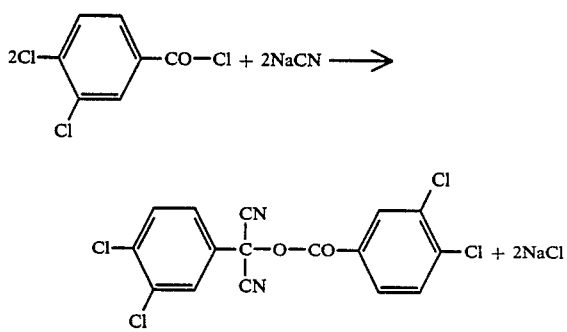

In the formulae (I) and (II), the substituent Ar preferably represents in each case substituted phenyl, naphthyl, pyridyl, thiazolyl, pyrimidinyl, thienyl or furyl.

Suitable substituents for the Ar radicals described above are preferably:

halogen (particularly Cl, Br or F) alkyl, alkoxy, halogenoalkyl, hydroxyl, halogenoalkoxy, alkylthio, amino, halogenoalkylthio, nitro, cyano, alkylsulphonyl, halogenoalkylsulphonyl, optionally halogen-substituted alkylenedioxy, alkoxyalkyl, halogenoalkoxyalkyl, carbonyl, carbalkoxy or the alkoxy-N=CH— radical.

Phenyl or pyridyl which is substituted by one or more of the following radicals, the substituents being identical or different, is particularly suitable for the substituents Ar:

Halogen, nitro, amino, CN, OH, $C_{1-4}$-alkyl, $C_{1-4}$-halogenoalkyl, $C_{1-4}$-alkoxy, $C_{1-4}$-halogenoalkoxy, methylenedioxy, ethylenedioxy, difluoromethylenedioxy, halogen-substituted ethylenedioxy, $C_{1-4}$-alkylthio, $C_{1-4}$-halogenoalkylthio, $C_{2-8}$-halogenoalkoxyalkyl, $C_{1-4}$-alkylsulphonyl, $C_{1-4}$-halogenoalkylsulphonyl, carbonyl, carbalkoxy and the $C_{1-4}$-alkoxy-N=CH— radical.

To a particular extent, Ar represents phenyl which is substituted by halogen, $C_{1-4}$-alkyl, $C_{1-4}$-alkoxy, $C_{1-4}$-halogenoalkoxy, $C_{1-4}$-halogenoalkyl, $NH_2$, $CH_3O$—N=CH— or $NO_2$.

Suitable alkali metal cyanides in the process according to the invention are preferably NaCN and KCN, and suitable aliphatic ketones are preferably those having 4 to 15 carbon atoms, where the following may be mentioned as examples:

Butanone, methyl isopropyl ketone, methyl propyl ketone, methyl butyl ketone, methyl isobutyl ketone, pinacoline, diethyl ketone, dipropyl ketone, 5-methyl-3-heptanone, diisobutyl ketone and 2-undecanone.

Methyl isobutyl ketone is a particularly preferred aliphatic ketone.

Suitable phase-transfer catalysts are, in particular quaternary ammonium salts, such as, for example, tetrabutylammonium bromide, triethylbenzylammonium chloride, octyltrimethylammonium chloride, dimethyl-dodecyl-benzylammonium chloride, tetraethylammonium chloride and tetrabutylammonium chloride.

The starting compounds of the formula (II) the alkali metal cyanides and the phase-transfer catalysts are known from the literature.

The process according to the invention is preferably carried out as follows:

The acyl chloride (II) and the quaternary ammonium salt (0.01 to 10 mol%) are initially introduced in the aliphatic ketone, and an aqueous alkali metal cyanide solution is added dropwise. At least 1 mol of cyanide is used per mol of acyl halide, but a slight excess of up to 20% of alkali metal cyanide is preferred.

The alkali metal cyanide is employed as the most concentrated aqueous solution possible. However, dilute solutions are likewise possible. Concentrations between 20 and 40 mol% are preferred.

The preferred temperature range is between 0° C. and 50° C., particularly preferably between 0° C. and 20° C.

Reaction duration: 15 minutes–12 hours, depending on the reactivity of the acyl halide employed. The dimeric acyl cyanide of the formula (I) is isolated by filtration or working-up of the mother liquor.

The reaction may be carried out at atmospheric pressure, but also at increased pressure. In general, the reaction is carried out at atmospheric pressure.

The substances prepared according to the invention are used for the preparation of insecticidal and acaricidal hydroxymalonic diamides (in this respect, cf. European Patent Specification No. 76,957).

Furthermore, the hydroxymalonic diamides thus obtained have a fungicidal action (cf. Dutch Application No. 6,704,966).

Example for the preparation of insecticidal and acaricidal hydroxymalonic acid diamides starting from the dimeric aromatic acyl cyanides by means of acid hydrolysis:

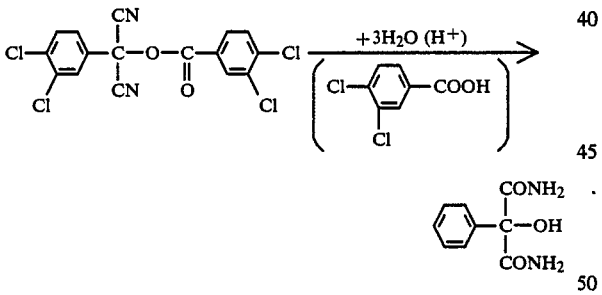

The other hydroxymalonic acid diamide end products can be prepared accordingly, thereby inserting the corresponding dimeric acyl cyanides.

PREPARATION EXAMPLE

EXAMPLE 1

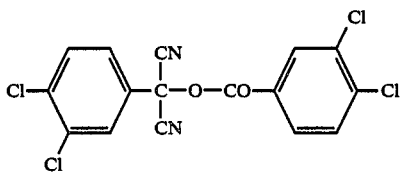

62.8 g (0.3 mol) of 3,4-dichlorobenzoyl chloride and 300 mg of triethylbenzylammonium chloride are placed in 250 ml of methyl isobutyl ketone. 15 g (0.308 mol) of sodium cyanide in 57 ml of water are added dropwise at 25° C. with stirring. The mixture is stirred for a further 10 hours at 20°–25° C. and filtered off. 86.3 g (71.9% of theory) of α,α-bis-cyano-3,4-dichloro-benzyl 3,4-dichlorobenzoate of melting point 110° C. are obtained.

EXAMPLE 2

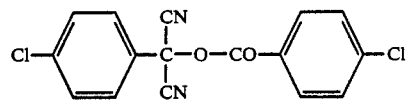

262.5 g (1.5 mols) of 4-chlorobenzoyl chloride and 2.5 g of tetrabutylammonium chloride are placed in 600 ml of methyl isobutyl ketone and cooled to 0° C. A solution of 75 g of sodium cyanide in 225 ml of water is added dropwise with cooling at a rate such that a temperature of 5° C. is not exceeded. 300 ml of water are subsequently added, and the mixture is stirred for a further 5 minutes, filtered and washed with methyl isobutyl ketone. After drying, 425 g (85.6% of theory) of α,α-bis-cyano-4-chloro-benzyl 4-chlorobenzoate are obtained. Melting point: 158°–159° C.

EXAMPLE 3

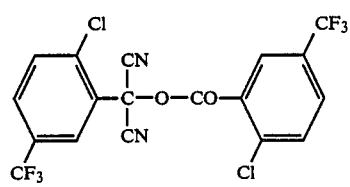

243 g of 2-chloro-5-trifluoromethylbenzoyl chloride and 1.8 g of tetrabutylammonium chloride are placed in 410 ml of butanone, and 50.2 g of sodium cyanide in 190 ml of water are added dropwise at room temperature. The mixture is stirred for a further 12 hours at room temperature, then filtered off under suction and washed with butanone.

Yield: 166 g of α,α-bis-cyano-2-chloro-5-trifluoromethylbenzyl 2-chloro-5-trifluoromethylbenzoate (72% of theory); melting point: 130° C.

EXAMPLE 4

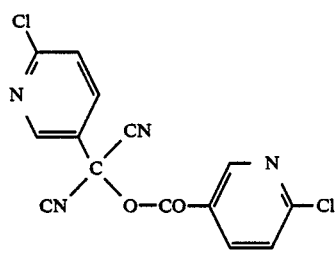

17.6 g (0.1 mol) of 2-chloro-pyridine-5-carbonyl chloride and 0.35 g (1 mmol) of tetrabutylammonium bromide are placed in 80 ml of methyl isobutyl ketone. 5 g (0.1024 mol) of sodium cyanide in 19 ml of water are then added dropwise at 20°–25° C. After 1.5 hours, a solid starts to precipitate. After a further 6 hours, this is filtered off under suction and washed with 30 ml of methyl isobutyl ketone. Yield: 13.1 g of 2-chloro-pyridine-5-carbonic acid-dicyano-(2-chloro-5-pyridyl)-methylester (78.7% of theory) of melting point 158° C.

The following dimeric acyl cyanides were also synthesized analogously to Example 1:

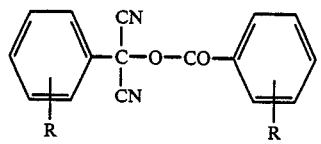

| Example | R | m.p. (°C.) | Yield (of theory) |
|---|---|---|---|
| 5 | 4-NO$_2$ | 179–180 | 97.8% |
| 6 | 2-OCH$_3$ | 150–151 | 59.5% |
| 7 | 4-Br | 153–154 | 87.6% |
| 8 | 4-C(CH$_3$)$_3$ | 123 | 54.8% |

It is understood that the specification and examples are illustrative but not limitative of the present invention and that other embodiments within the spirit and scope of the invention will suggest themselves to those skilled in the art.

We claim:

1. In a process for the preparation of a dimeric aromatic acyl cyanide of the formula

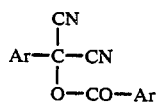

in which

Ar is phenyl, naphthyl, pyridyl, thiazolyl, pyrimidinyl, thienyl or furyl which is in each case optionally substituted by halogen, alkyl, alkoxy, halogenoalkyl, hydroxyl, halogenoalkoxy, alkylthio, amino, halogenoalkylthio, nitro, cyano, alkylsulphonyl, halogenoalkylsulphonyl, optionally halogen-substituted alkylenedioxy, alkoxyalkyl, halogenoalkoxyalkyl, carboxyl, carbalkoxy or alkoxy-N=CH—, comprising reacting an acyl halide of the formula Ar—CO—Hal in which Hal is fluorine, chlorine or bromine, with an alkali metal cyanide the improvement comprising conducting the reaction in a two-phase system comprising water and a water-immiscible or only sparingly water-miscible aliphatic ketone, and in the presence of a phase-transfer catalyst selected from the group consisting of tetrabutylammonium bromide, triethylbenzylammonium chloride, octyltrimethylammonium chloride, dimethyl-dodecylbenzylammonium chloride, tetramethylammonium chloride and tetrabutylammonium chloride.

2. A process according to claim 1, wherein the aliphatic ketone has 4 to 14 carbon atoms.

3. A process according to claim 1, wherein the aliphatic ketone is selected from the group consisting of butanone, methyl isopropyl ketone, methyl propyl ketone, methyl butyl ketone, methyl isobutyl ketone, pinacoline, diethyl ketone, dipropyl ketone, 5-methyl-3-heptanone, diisobutyl ketone and 2-undecanone.

4. A process according to claim 1, wherein about 1 to 1.2 mols of alkali metal cyanide are employed per mol of acyl halide.

5. A process according to claim 1, wherein the reaction is carried out at a temperature from about 0° C. to 50° C.

6. A process according to claim 1, wherein the phase transfer catalyst is selected from the group consisting of tetrabutylammonium bromide, triethylbenzylammonium chloride, octyltrimethylammonium chloride, dimethyl-dodecylbenzylammonium chloride, tetramethylammonium chloride and tetrabutylammonium chloride, the aliphatic ketone is selected from the group consisting of butanone, methyl isopropyl ketone, methyl propyl ketone, methyl butyl ketone, methyl isobutyl ketone, pinacoline, diethyl ketone, dipropyl ketone, 5-methyl-3-heptanone, diisobutyl ketone and 2-undecanone, about 1 to 1.2 mols of alkali metal cyanide are employed per mol of acyl halide, and the reaction is carried out at a temperature from about 0° C. to 50° C.

* * * * *